United States Patent [19]

Cox

[11] 4,342,392
[45] Aug. 3, 1982

[54] WRAP FOR STERILE ARTICLES

[75] Inventor: Lloyd A. Cox, Memphis, Tenn.

[73] Assignee: The Buckeye Cellulose Corporation, Cincinnati, Ohio

[21] Appl. No.: 73,971

[22] Filed: Sep. 10, 1979

[51] Int. Cl.³ .............................................. A61F 15/00
[52] U.S. Cl. ................................ 206/438; 128/132 D; 229/75; 229/87 A
[58] Field of Search ............................. 206/438, 440; 128/132 D; 229/87 A, 75, 76

[56] References Cited

U.S. PATENT DOCUMENTS

| | | |
|---|---|---|
| 2,997,166 | 8/1961 | Pratt . |
| 3,119,495 | 1/1964 | Pratt . |
| 3,148,771 | 9/1964 | Miller . |
| 3,225,920 | 12/1965 | Reilly . |
| 3,419,136 | 12/1968 | Pratt . |
| 3,680,772 | 8/1972 | Hovner ............................ 206/438 |
| 3,742,944 | 7/1973 | Sease . |
| 3,780,857 | 12/1973 | Rosano ............................. 206/438 |
| 3,783,862 | 1/1974 | Schrading ..................... 128/132 P |
| 3,795,309 | 3/1974 | Link .................................. 206/438 |
| 4,015,845 | 5/1976 | Collins . |
| 4,099,614 | 7/1978 | Heissenberger .................... 206/438 |

FOREIGN PATENT DOCUMENTS 2815046 11/1978 Fed. Rep. of Germany ...... 206/438

*Primary Examiner*—Herbert F. Ross
*Attorney, Agent, or Firm*—Milton B. Graff, IV; John V. Gorman; Richard C. Witte

[57] ABSTRACT

Disclosed herein is a wrap for a sterile article. The wrap is a sheet which encases the article to be wrapped by means of at least two inward folds, forming panels atop the article to be shielded. One of these panels has attached to it a member which extends underneath the package from a point on the panel spaced from its inward fold line so that the article can be unwrapped by reaching under the wrapped article and grabbing the member. By pulling the member towards the user with the package oriented with the panel that is attached to the member away from the user, the package can be unwrapped without reaching over and contaminating the exposed sterile article.

10 Claims, 7 Drawing Figures

WRAP FOR STERILE ARTICLES

TECHNICAL FIELD

This invention relates to a wrap for enclosing an article before and after sterilization and until use. More particularly it is suitable for wrapping folded surgical gowns and drapes.

BACKGROUND ART

In the past sterile articles including surgical drapes and gowns have been folded and then wrapped prior to sterilization, with a sheet of paper or fabric folded around the article in what is known as triangular fold. An example of a triangularly folded wrap can be found in U.S. Pat. No. 4,051,845 issued to Collins on Oct. 4, 1977, FIGS. 1-5.

The prior art also includes some packages for sterile articles which are rectangularly folded. By rectangularly folded it is meant that an edge of a starting sheet is folded over the item around a fold line parallel to the edge being folded. A rectangular wrap, as used herein, refers to a package formed from a rectangular sheet solely by rectangular folds. In U.S. Pat. No. 4,099,614 issued to Heissenberger on July 11, 1978 a rectangularly wrapped glove package is disclosed which is said to be easily automated. U.S. Pat. No. 3,148,711 issued on Sept. 15, 1964 to Miller and U.S. Pat. No. 3,119,495 issued on Jan. 28, 1964 to Pratt also disclose rectangularly wrapped sterile articles. The Pratt and Miller packages use adhesive to secure the sides closed. The packages are unwrapped by pulling flaps which are folded into the wrap.

It has long been a goal in the field of packaging of sterile articles to provide a wrap which is easily accomplished and easily removed without contaminating the sterile contents by touching them or reaching into the sterile field during unwrapping. The sterile field, as used herein, is descriptive of a region of space during a period of time. More specifically, it is the region of space above a sterile surface for the period of time which the surface is exposed beneath the space, and for a short time prior to its exposure. Refraining from entering the sterile field with non-sterile objects, insures that airborne contamination will not be released at a time and location which make it probable that the contaminants will settle on a sterile surface.

The triangularly folded wraps fail in that they are not easily adapted to mechanized folding, involve extra unwrapping steps and require that the unwrapper reach into the sterile field or turn the package to avoid reaching into the sterile field. Turning the package or reaching into the sterile field or moving to a different position to avoid reaching into the field or turning the product is inconvenient and results in excessive air movement which is conductive to developing airborne contamination in the sterile field which may settle on the sterile article.

The prior rectangularly folded packages also require the unwrapper to reach into the sterile field. In addition, the pouches of Pratt and Miller are not amenable to removal of contents without contact.

DISCLOSURE OF THE INVENTION

This invention relates to a wrap for a sterile article which permits unfolding of the wrap from one side without reaching into the article's sterile field. The wrap has a bottom panel with top, bottom and side edges which is situated underneath the sterile article. The wrap also includes a first panel folded inwardly on a first fold line corresponding to the top edge of the bottom panel with the first fold line corresponding to the top edge of the first panel. The first panel is superimposed atop the article and the bottom panel. The wrap also includes a second panel folded outwardly on a second fold line corresponding to the bottom edge of the first panel. The second panel is superimposed over the first panel with the bottom edge of the second panel corresponding to the second fold line. A third panel is folded underneath the bottom panel on a third fold line corresponding to the top edge of the second panel with the top edge corresponding to the third fold line. Finally, a fourth panel is folded inwardly atop the sterile article on a fourth fold line corresponding to the bottom edge of the bottom panel so that the fourth panel is superimposed on top of the article and the bottom panel.

DETAILED DESCRIPTION OF THE INVENTION

Figure 1:
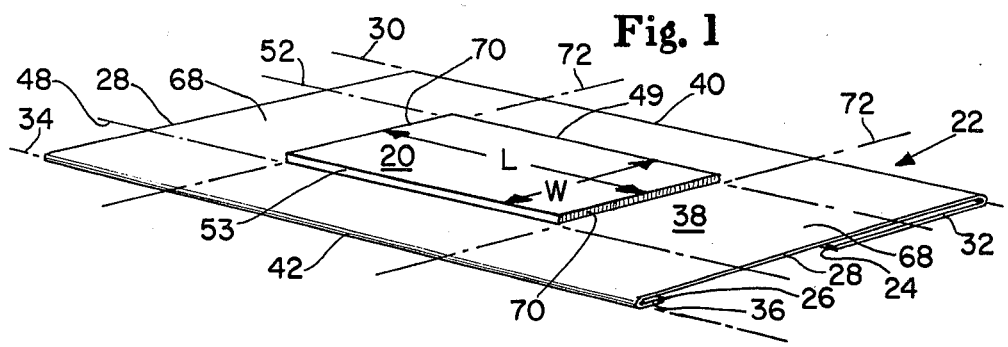
FIG. 1 is an elevated perspective view of the sterile article and the wrap of the present invention before the article is wrapped.

Referring to the drawings wherein like reference characters are utilized for like parts throughout the several views, there is illustrated in FIG. 1 a product 20 to be wrapped with a sheet 22 which preferably is rectangular. The sheet 22 may be made of any flexible sheet material including film, tissue, paper, or woven or nonwoven fabric.

As used herein the term "fold" describes the act of producing a connection between two generally flat panels not in the same plane including bending a sheet composed of at least two integrally connected panels, and securing with adhesive or by heat sealing two separate panels at an angle with respect to one another. The term "fold line" as used herein denotes the line of connection between the two panels in different planes. In general it is preferred that all folds herein be rectangular folds produced by bending an integral sheet since such folds are easily accomplished by automated machinery.

Sheet 22 has an upper edge 24, a lower edge 26 and side edges 28. A portion of the sheet adjacent upper edge 24 is folded, preferably by a rectangular fold, along a fold line 30 to form unwrapping flap 32. A portion of sheet 22 adjacent lower edge 26 is folded, preferably by a rectangular fold, towards unwrapping flap 32, along fold line 34 to form a protective flap 36. The fold lines 30 and 34 together with sides edges 28 define main panel 38 having a top edge 40 corresponding to fold line 30 and a bottom edge 42 corresponding to fold line 34. As shown in FIG. 1 the unwrapping flap 32 is then defined as the portion of sheet 22 between top edge 40, side edges 28 and upper edge 24. The protective flap 36 is defined as the portion of sheet 22 between side edges 28, lower edge 26 and bottom edge 42. Unwrapping flap 32 and protective flap 36 both lie on the side of main panel 38 not touching the product 20.

Figure 2:
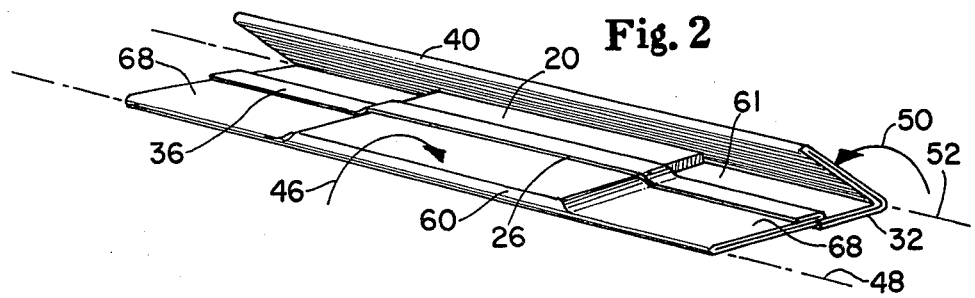
FIG. 2 is an elevated perspective view of the wrap being folded around the sterile article.

In FIG. 2 the sheet 22 is shown about to envelop product 20 centered between side edges 28 on main panel 38 but located slightly closer to bottom edge 42 than to top edge 40. The sheet is first folded around the product 20 by a fold 46, preferably a rectangular fold, shown already completed and indicated by an arrow in FIG. 2, around fold line 48, preferably parallel to bottom edge 42 of main panel 38. Then a fold 50, preferably a rectangular fold, shown partially completed with the direction of the fold indicated by an arrow in FIG. 2, is made around fold line 52, preferably parallel to top edge 40 of main panel 38. When the product 20 is rectangular as is the one shown in the figures, each fold line 48 and 52 is adjacent and parallel to an edge of the product 20. The fold 50 around fold line 52 creates a doubled panel 54, shown in FIG. 3, situated over the product 20. The panel 54 extends from the top edge 40 of the main panel 38 to upper exterior edge 56 created by the fold 50 around fold line 52 and includes a portion of flap 32 and a portion of main panel 38. Similarly the fold 46 around fold line 48 creates a fourth panel 58 atop the product 20. The fourth panel 58 extends from the bottom edge 42 of the main panel 38 to the edge 60 created by the fold 46 around fold line 48 but does not include flap 36. Together fold lines 48 and 52 define a bottom panel 61 between them, which is a part of main panel 38 and serves to cover the lower side of the product 20. The folds 46 and 50 are both inward folds in that they progress toward the product 20 while the folds forming unwrapping flap 32 and protective flap 36 are conversely outward folds since the respective flaps 32 and 36 are directed away from the product 20.

Figure 3:
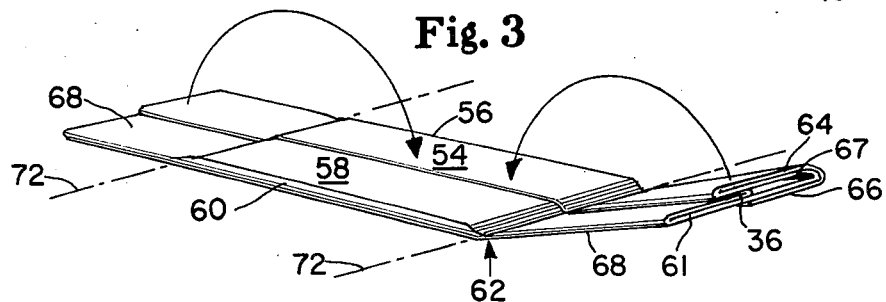
FIG. 3 is an elevated perspective view of the first folded tube showing how the side regions are to be folded.

The first folded tube 62 which results is shown in FIG. 3. It can be seen that doubled panel 54 is situated partially overlapping fourth panel 58 and completely covering protective flap 36. Alternatively the fourth panel 58 could be folded atop doubled panel 54. It can be seen that the unwrapping flap 32 has been divided by the fold 50 around fold line 52 into second panel 64 which is situated over the product 20 and third panel 66 situated under product 20 facing bottom panel 61. Second panel 64 is defined as the region between side edges 28, upper exterior edge 56 or fold line 52 and top edge 40. Third panel 66 is defined by side edges 28, upper exterior edge 56 or fold line 52 and upper edge 24 of sheet 22. Doubled panel 54 is made up of first panel 67 and second panel 64. First panel 67, identical in size to second panel 64, lies between product 20 and second panel 64 which completely overlaps first panel 67. First panel 67, which is a part of main panel 38, is bounded by bottom panel 61 at upper exterior edge 56 and by the second panel 64 at top edge 40 of main panel 38. Thus bottom panel 61 is connected to first panel 67 which is inwardly folded and connected to second panel 64, outwardly folded and, in turn, connected to third panel 66.

The preferred relative sizes of the panels, flaps, and regions which make up the first folded tube 62 with respect to the product 20 can be gauged from FIG. 1. In FIG. 1 the width W, the dimension perpendicular to fold line 52, and length L, the dimension parallel to fold line 52, of the product 20 are shown. It can be seen that the third panel 66 of unwrapping flap 32 is of a length equal to about one quarter of the width of the product 20 or conveniently from about 2 to about 15 centimeters, while first panel 67 and second panel 64 cover slightly more than half the width of the product 20. The protective flap 36 on the other hand is much shorter and, in general, may conveniently be approximately 1 to 4 centimeters in length.

It can be seen in FIGS. 1 and 2 that a side region 68 extends beyond each lateral edge 70 of the product. Preferably each side region 68 extends a distance of slightly more than one half of the length to a distance equal to the length of the product 20 so that side regions 68 are of sufficient length to overlap one another atop the product 20. In an alternate embodiment shown in FIG. 5 side regions 68 extend beyond the lateral edges 70 of the product a distance from one fifth to one half of the length of the product, most preferably extending a distance approximately one quarter of the length of the product beyond each edge 70.

Figure 4:
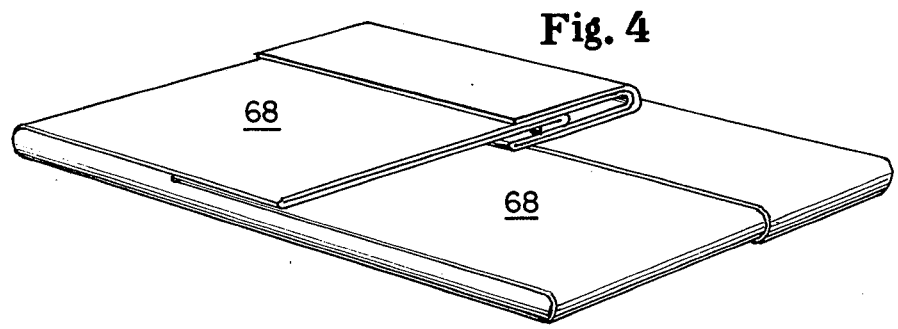
FIG. 4 is an enlarged, elevated, perspective view of a wrapped sterile article.

The folding of the sheet 22 is completed by folding side regions 68 inwardly on top of the product around fold lines 72, preferably by rectangular folds parallel to the side edges 28 of sheet 22, as indicated by arrows in FIG. 3. When the product 20 is rectangular, as pictured, each fold line 72 is parallel to and adjacent an edge 70 of product 20. Since the regions 68 substantially overlap one another when folded as shown in FIG. 4, no securement of the regions 68 to the rest of the wrap is normally necessary since the weight of the regions 68 tends to maintain them in position. In the alternate embodiment shown in FIG. 5, after folding, each side region 68 is secured to second panel 64 of the sheet by a tape strip 76. Alternatively, releasable glue spots (not shown) can be used between second panel 64 and each side region 68 instead of tape strips 76.

Figure 5:
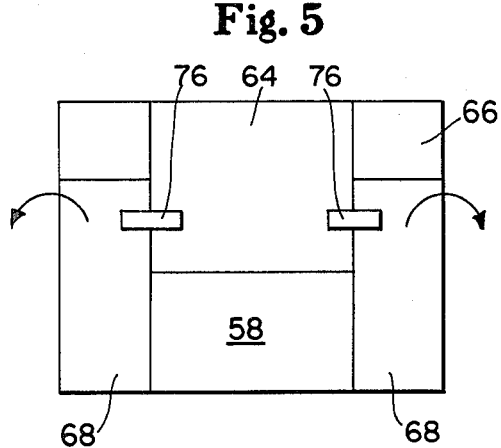
FIG. 5 is a top plan view of another embodiment of a wrapped sterile product of the present invention.
Figure 6:
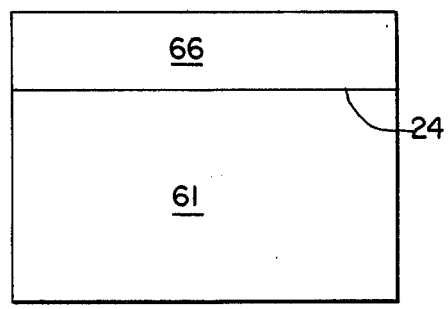
FIG. 6 is a bottom plan view of the wrapped sterile articles shown in FIGS. 4 and 5.

Finished rectangularly wrapped products are shown in FIGS. 4 and 5. Except for the length and method of securing the regions 68, the products pictured in FIGS. 4 and 5 are identical. FIG. 6 shows the underside (which is identical for the embodiments shown in FIGS. 4 and 5) of the folded sheet 22 having third panel 66 of unwrapping flap 32 unattached. While the rectangular folding and sizing of the regions 68 shown in either FIG. 4 or 5 is preferred, any conventional method may be used to fold and attach the side regions 68.

The wrapped sterile product may in turn be enclosed within still another package which preferably is a sealed plastic bag. After the bag containing the wrapped product is subjected to sterilization, the contents are ready for use.

The sheet 22 can be unwrapped without contamination by a surgical assistant who need not be surgically sterile. First, tape strips 76 if present are broken and side regions 68 are returned by the outward folds indicated by arrows in FIG. 5, around fold lines 72, to the position shown in FIG. 3 which represents the first folded tube 62. By grasping each side region 68 over fourth panel 58 when outwardly folding the side regions 68, the unwrapper can avoid ever reaching into the sterile field of the product 20.

Figure 7:
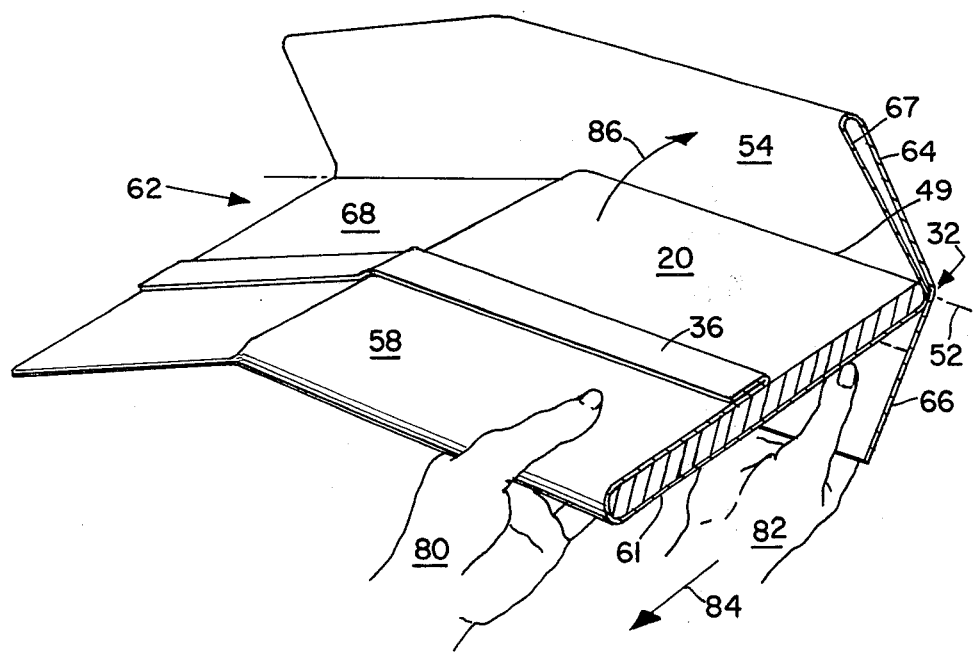
FIG. 7 is an enlarged, cut away, elevated perspective view of the first folded tube shown in FIG. 3 in the process of being unfolded.

As shown in FIG. 7, the party unfolding the wrap then supports the first folded tube 62 between the thumb and forefinger (not shown) of one hand 80 clamping the product 20 between fourth panel 58 and bottom panel 61. The first folded tube 62 is then dismantled by reaching under the first folded tube 62 with the other hand indicated as 82 and grasping third panel 66 between the thumb and forefinger (not shown). The third panel 66 is pulled toward the unwrapper's body as indicated by the arrow 84 in FIG. 7. This pulling force is transmitted by third panel 66 to second panel 64 to first panel 67 causing doubled panel 54 to rotate outwardly around fold line 52 or edge 49 of product 20, effectively reversing fold 50, as indicated by arrow 86. The doubled panel 54 falls below the supported product 20 which now is allowed to slide out on to a sterile surface from between fourth panel 58 and bottom panel 61 by tilting the far end of the product downwardly and loosening the grip of hand 80. The unwrapper is left holding the sheet 22 in hand 80. Since a sterile surface is not exposed beneath panel 58, a sterile field need not be maintained over fourth panel 58; therefore, the region above panel 58 serves as a convenient space for grasping and unfolding side regions 68. The product 20 then can be unfolded and used by sterile personnel without having been contaminated by being touched or having its sterile field violated during unwrapping.

In an alternate method not illustrated, the wrapped product 20 is grasped with the hand 80 rotated so that the thumb is on the underside touching bottom panel 61 and the forefinger is on the upper side touching fourth panel 58. The end of the forefinger of hand 80 is then nestled between protective flap 36 and fourth panel 58, the flap 36 serving as a stop to prevent accidental contact with the product 20 by the forefinger.

While particular embodiments of the present invention have been illustrated and described, it will be obvious to those skilled in the art that various changes and modifications can be made without departing from the spirit and scope of the invention and it is intended to cover, in the appended claims, all such modifications that are within the scope of this invention.

What is claimed is:

1. A wrap for a sterile article which permits unfolding of the wrap from one side without reaching into the article's sterile field comprising a bottom panel having top, bottom and side edges and situated underneath said sterile article; a first panel folded inwardly on a first fold line corresponding to the top edge of said bottom panel, said first panel having top, bottom, and side edges, said first fold line corresponding to said top edge of said first panel and said first panel being superimposed atop said article and said bottom panel; a second panel folded outwardly on a second fold line corresponding to the bottom edge of said first panel, said second panel having top, bottom and side edges, and being superimposed over said first panel, said bottom edge of said second panel corresponding to said second fold line; a third panel folded underneath said bottom panel on a third fold line corresponding to the top edge of said second panel, said third panel having top, bottom and side edges, said top edge of said third panel corresponding to said third fold line; a fourth panel folded inwardly atop said sterile article on a fourth fold line corresponding to the bottom edge of said bottom panel, and being superimposed on top of said article and said bottom panel.

2. The wrap of claim 1 being an integral rectangular sheet of flexible material all of said folds being rectangular folds.

3. The wrap of claim 2 having side regions extending beyond said article and being folded atop said article, said side regions having ends.

4. The wrap of claim 3 wherein said side regions overlap one another.

5. The wrap of claim 3 wherein the end of each side region is attached to said wrap over said article.

6. The wrap of claim 5 wherein said attachment is by releasable tape strips.

7. The wrap of claim 5 wherein said attachment is by releasable glue spots.

8. The wrap of claim 1 wherein said first panel and said fourth panel are in overlapping relationship.

9. The wrap of claim 1 wherein said fourth panel has an outwardly folded protective flap.

10. The wrap of claim 2 wherein said wrap is a rectangular wrap.

* * * * *